(12) United States Patent
Wesemann et al.

(10) Patent No.: US 9,553,276 B2
(45) Date of Patent: Jan. 24, 2017

(54) COMPLEX COMPOUNDS HAVING TETRADENTATE LIGANDS AND THE USE THEREOF IN THE OPTO-ELECTRONIC FIELD

(75) Inventors: Lars Wesemann, Tuebingen (DE); Hermann August Mayer, Tuebingen (DE); Hartmut Schubert, Bodelshausen (DE); Sophie Wernitz, Köln (DE)

(73) Assignee: Merck Patent GmbH (DE)

( * ) Notice: Subject to any disclaimer, the term of this patent is extended or adjusted under 35 U.S.C. 154(b) by 0 days.

(21) Appl. No.: 14/234,809

(22) PCT Filed: Jul. 18, 2012

(86) PCT No.: PCT/EP2012/064125
§ 371 (c)(1),
(2), (4) Date: Feb. 26, 2014

(87) PCT Pub. No.: WO2013/014048
PCT Pub. Date: Jan. 31, 2013

(65) Prior Publication Data
US 2014/0186984 A1 Jul. 3, 2014

(30) Foreign Application Priority Data
Jul. 26, 2011 (DE) .................. 10 2011 079 857

(51) Int. Cl.
*H01L 21/00* (2006.01)
*H01L 51/50* (2006.01)
(Continued)

(52) U.S. Cl.
CPC ............ *H01L 51/50* (2013.01); *C07F 9/5045* (2013.01); *C07F 15/0033* (2013.01);
(Continued)

(58) Field of Classification Search
CPC ............... H01L 51/009; H01L 51/0084; H01L 51/0087; H01L 51/0091; H01L 51/50
(Continued)

(56) References Cited

U.S. PATENT DOCUMENTS 6,963,005 B2    11/2005  Lecloux et al.
7,683,183 B2     3/2010  Peters et al.
(Continued)

FOREIGN PATENT DOCUMENTS

CN    101747375 A    6/2010
DE    102008033563 A1    1/2010
(Continued)

OTHER PUBLICATIONS

Cheng, Yi-Ming, et al., "Rational Design of Chelating Phosphine Functionalized Os(II) Emitters and Fabrication of Orange Polymer Light-Emitting Diodes Using Solution Process", Adv. Funct. Mater., vol. 18, (2008), pp. 83-194.
(Continued)

*Primary Examiner* — Brook Kebede
(74) *Attorney, Agent, or Firm* — Drinker Biddle & Reath LLP

(57) ABSTRACT

The invention describes electronic devices comprising a metal complex compound having at least one tetradentate ligand having N and/or P donors, in particular a ligand having a PPPP, NNNN, PNNP or NPPN structure, and uses of a complex of this type in the electronic field and for the generation of light.

17 Claims, 3 Drawing Sheets

(51) Int. Cl.
  *C09K 11/06* (2006.01)
  *H01L 51/00* (2006.01)
  *C07F 9/50* (2006.01)
  *C07F 15/00* (2006.01)

(52) U.S. Cl.
  CPC ...... *C07F 15/0073* (2013.01); *C07F 15/0093* (2013.01); *C09K 11/06* (2013.01); *H01L 51/009* (2013.01); *H01L 51/0084* (2013.01); *H01L 51/0087* (2013.01); *H01L 51/0091* (2013.01); *C09K 2211/1007* (2013.01); *C09K 2211/185* (2013.01); *C09K 2211/187* (2013.01); *C09K 2211/188* (2013.01); *Y02E 10/549* (2013.01); *Y02P 70/521* (2015.11)

(58) Field of Classification Search
  USPC .............................................. 438/46; 257/40
  See application file for complete search history.

(56) References Cited

U.S. PATENT DOCUMENTS

| | | | |
|---|---|---|---|
| 2002/0048689 A1 | 4/2002 | Igarashi et al. | |
| 2005/0244672 A1* | 11/2005 | Che | C09K 11/06 428/690 |
| 2006/0202197 A1* | 9/2006 | Nakayama et al. | 257/40 |
| 2006/0264625 A1* | 11/2006 | Nakayama et al. | 544/225 |
| 2007/0111026 A1 | 5/2007 | Deaton et al. | |
| 2007/0148495 A1* | 6/2007 | Che | C09K 11/06 428/690 |
| 2007/0265473 A1 | 11/2007 | Becker et al. | |
| 2008/0036370 A1 | 2/2008 | Noh et al. | |
| 2010/0026174 A1 | 2/2010 | Igarashi et al. | |
| 2010/0227974 A1 | 9/2010 | Schulte et al. | |
| 2011/0108769 A1 | 5/2011 | Yersin et al. | |
| 2011/0144366 A1 | 6/2011 | Stoessel et al. | |
| 2011/0155954 A1 | 6/2011 | Yersin et al. | |

FOREIGN PATENT DOCUMENTS

| | | |
|---|---|---|
| EP | 1424350 | 6/2004 |
| JP | 2003212886 A | 7/2003 |
| JP | 2009260286 | 11/2009 |
| WO | WO-2004/041901 | 5/2004 |
| WO | WO-2005/118606 A1 | 12/2005 |
| WO | WO-2008/019744 A1 | 2/2008 |
| WO | WO-2010006681 A1 | 1/2010 |
| WO | WO-2011063083 A1 | 5/2011 |

OTHER PUBLICATIONS

Deaton, Joseph C., et al., "E-Type Delayed Fluorescence of a Phosphine-Supported $Cu_2(\mu-NAr_2)_2$ Diamond Core: Harvesting Singlet and Triplet Excitons in OLEDsII", J. Am. Chem. Soc., vol. 132, (2010), pp. 9499-9508.
Kui, Steven C.F., et al., "Platinum(II) Complexes with □-Conjugated, Naphthyl-Substituted, Cyclometalated Ligands (RC□N□N): Structures and Photo- and Electroluminescence", Chem. Eur. J., vol. 13, (2007), pp. 417-435.
Miller, Alexander J.M., et al., "Long-Lived and Efficient Emission from Mononuclear Amidophosphine Complexes of Copper", Inorganic Chemistry, vol. 46, No. 18, (2007), pp. 7244-7246.
Moudam, Omar, et al., "Electrophosphorescent Homo- and Heteroleptic Copper(I) Complexes Prepared from Various Bis-Phosphine Ligands", Chem. Commun., (2007), pp. 3077-3079.
International Search Report for PCT/EP2012/064125 mailed Oct. 23, 2012.
U.S. Appl. No. 14/234,710, filed Jan. 24, 2014, Wesemann et al.
U.S. Appl. No. 14/234,781, filed Jan. 24, 2014, Wesemann et al.
U.S. Appl. No. 14/234,857, filed Jan. 24, 2014, Wesemann et al.
English translation of Office Action for corresponding Japanese Application No. 2014-522038 mailed Aug. 2, 2016.

* cited by examiner

COMPLEX COMPOUNDS HAVING TETRADENTATE LIGANDS AND THE USE THEREOF IN THE OPTO-ELECTRONIC FIELD

CROSS-REFERENCE TO RELATED APPLICATIONS

This application is a national stage application (under 35 U.S.C. §371) of PCT/EP2012/064125, filed Jul. 18, 2012, which claims benefit of German application 10 2011 079 857.9, filed Jul. 26, 2011.

The present invention relates to electronic devices, such as organic electroluminescent devices (OLEDs), light-emitting electrochemical cells (LEECs), organic solar cells (OSCs), organic field-effect transistors and organic lasers, which comprise organotransition metal complex compounds as light emitters and/or light absorbers. Some particularly suitable complex compounds and the use thereof in the opto-electronic field are described.

Organotransition metal complex compounds are important building blocks for opto-electronic devices, such as organic solar cells or organic electroluminescent devices. This applies, in particular, to compounds which are able to function as triplet emitters. In the case of triplet emission, also known as phosphorescence, high internal quantum yields of up to 100% can be achieved if the singlet state, which is also excited and is energetically above the triplet state, is able to relax completely into the triplet state and radiation-free competing processes remain unimportant. However, many triplet emitters which are basically suitable for opto-electronic applications have the disadvantage of a long emission lifetime, which can result in a drop in efficiency, for example in OLED devices provided with emitters of this type.

Yersin et al. in WO 2010/006681 A1 have proposed organotransition metal compounds which have a very small energetic separation $\Delta E$ between the lowest triplet state and the higher singlet state and in which efficient re-occupation from the efficiently occupied $T_1$ state into the $S_1$ state can therefore already occur at room temperature. This re-occupation opens a fast emission channel from the short-lived $S_1$ state, which enables the total emission lifetime to be significantly reduced. Complexes containing metal centres having a $d^8$-electron configuration, i.e., in particular, based on the very expensive metals rhodium, iridium, palladium, platinum and gold, have been described as particularly suitable for this purpose.

The present invention was based on the object of providing organotransition metal complex compounds based on readily available and very inexpensive transition metals which are ideally at least equal to the organotransition metal complex compounds known from WO 2010/006681 in their physical properties, such as colour purity, emission decay time and quantum efficiency.

The present invention relates to the electronic device comprising a metal complex having at least one tetradentate ligand having N and/or P donors, in particular a ligand having a PPPP, NNNN, PNNP or NPPN structure. The present invention likewise relates to a process for the generation of light of a certain wavelength, comprising the step of the provision of a metal complex having a tetradentate ligand having N and/or P donors, in particular a ligand having a PNNP or NPPN structure;

a process for the generation of blue emission using a metal complex having a tetradentate ligand having N and/or P donors, in particular a ligand having a PNNP or NPPN structure and a process for the production of an electronic device according to the invention, characterised in that a metal complex compound having at least one ligand of the formula I is printed onto a substrate.

Preferred embodiments of the device according to the invention are a) characterised in that the ligand has the general formula I

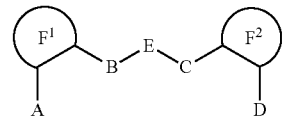

in which
A, B, C and D are, independently of one another, P or N, where the valences of N or P may be at least partially saturated by one or two atom(s) and/or radical(s), in particular from the group comprising hydrogen, halogen, R—, RO—, RS—, RCO—, RCOO—, RNH—, $R_2N$—, RCONR— and —$Si(R)_x(OR)_{3-x}$, where R=a $C_1$-$C_{40}$-hydrocarbon and X=1, 2 or 3, E is a bridge atom from the group with oxygen, sulfur, carbon, silicon or boron, to which one or two atom(s) and/or radical(s), in particular from the group with hydrogen, halogen, —CN, R—, RO—, RS—, RCO—, RCOO—, RNH—, $R_2N$—, RCONR— and —$Si(R)_x(OR)_{3-x}$, where R=the $C_1$-$C_{40}$-hydrocarbon and X=1, 2 or 3, may optionally be bonded and $F^1$ and $F^2$ are ring systems of an aromatic or non-aromatic nature, where two adjacent ring atoms form the bridge between A and B and between C and D.

b) characterised in that the ligand has the formula II

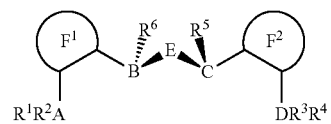

in which
A, B, C, D, $F^1$ and $F^2$ are defined as in formula I
$R^1$ to $R^6$ are, if they are bonded to a P, independently of one another, an atom or radical from the group comprising hydrogen, a halogen, R—, RO—, RS—, RCO—, RCOO—, RNH—, $R_2N$—, RCONR— and —$Si(R)_x(OR)_{3-x}$, where R=the $C_1$-$C_{40}$-hydrocarbon and X=1, 2 or 3, $R^1$ to $R^6$ are, if they are bonded to an N, independently of one another, an atom or radical from the group with H, the $C_1$-$C_{40}$-hydrocarbon R and the silyl radical —$Si(R)_x(OR)_{3-x}$, E is a bridge atom from the group with oxygen, sulfur, carbon, silicon or boron, where
one or two atoms and/or radicals from the group with hydrogen, halogen, —CN, R—, RO—, RS—, RCO—, RCOO—, RNH—, $R_2N$—, RCONR— and —$Si(R)_x(OR)_{3-x}$, where R=the $C_1$-$C_{40}$-hydrocarbon and X=1, 2 or 3, are optionally bonded to the carbon, two radicals R— and/or RO—, where R=the $C_1$-$C_{40}$-hydrocarbon, are optionally bonded to the silicon or one or two atoms and/or radicals from the group with halogen, R—, RO—, RS—, RCO—, RCOO—, RNH—, $R_2$N—, RCONR— and —Si(R)$_x$(OR)$_{3-x}$, where R=the $C_1$-$C_{40}$-hydrocarbon and X=1, 2 or 3, are optionally bonded to the boron.

c) characterised in that the ligand has the formula III

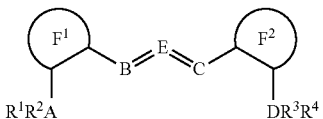

in which A, B, C, D, $R^1$ to $R^4$, $F^1$ and $F^2$ are defined as in formula II and E is a carbon atom, where an atom or radical from the group with hydrogen, halogen, —CN, R—, RO—, RS—, RCO—, RCOO—, RNH—, $R_2$N—, RCONR— and —Si(R)$_x$(OR)$_{3-x}$, where R=the $C_1$-$C_{40}$-hydrocarbon and X=1, 2 or 3, is optionally bonded to the carbon.

d) characterised in that the $C_1$- to $C_{40}$-hydrocarbon R is an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical, each of which may, in preferred embodiments, have one or more halogen, hydroxyl, thiol, carbonyl, keto, carboxyl, cyano, sulfone, nitro, amino and/or imino functions.

e) characterised in that $F^1$ and/or $F^2$ are a cycloalkyl, cycloalkenyl, cycloalkynyl, aryl, heteroaryl, aralkyl and/or heteroaralkyl radical.

f) characterised in that A and/or D are ring atoms of a ring system of an aromatic or non-aromatic nature.

g) characterised in that the metal complex is mononuclear or polynuclear, preferably has between two and six metal centres.

h) characterised in that the metal complex is a Cu, Ag, Au, Pd, Pt, Rh, Ir, Re, Os, Mo, W or Zn complex or the complex contains at least one of these metals.

i) a characterised in that the metal complex has the formula IV

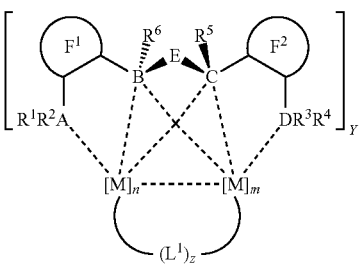

in which

A, B, C, D, $R^1$ to $R^6$, E, $F^1$ and $F^2$ are defined as in formula II, $[M]_n$ and $[M]_m$ represent complex fragments where M=Cu, Ag, Au, Pd, Pt, Rh, Ir, Re, Os, Mo, W or Zn and n, m are an integer between 1 and 6, Y is an integer between 1 and 8, $L^1$ is a bridging and/or non-bridging ligand and Z is an integer between 1 and 24.

j) characterised in that the metal complex has the formula V

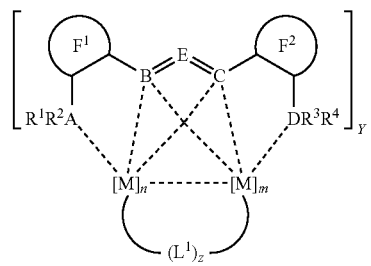

in which

A, B, C, D, $R^1$ to $R^4$, E, $F^1$ and $F^2$ are defined as in formula III, $[M]_{n,m}$, Y, L' and Z are defined as in formula IV.

k) selected from the group consisting of organic electroluminescent devices (OLEDs), light-emitting electrochemical cells (LEECs), organic solar cells (OSCs), organic field-effect transistors and organic lasers.

l) characterised in that it comprises the metal complex as constituent of an emitter layer, where the proportion of the metal complex in the emitter layer is preferably between 0.1 and 50% by weight.

m) characterised in that it comprises the metal complex as constituent of an absorber layer, where the proportion of the metal complex in the absorber layer is preferably between 30 and 100% by weight.

The wording of all claims is hereby incorporated into this description by way of reference.

Figure 1:
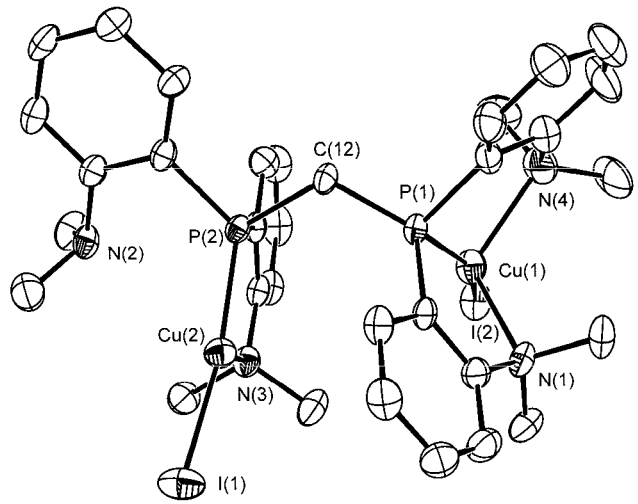
FIGS. 1 to 5 show the spatial structures of copper complexes (1) to (5) determined by means of X-ray diffractometry An electronic device according to the invention is distinguished by the fact that it comprises a metal complex having at least one tetradentate ligand having N and/or P donors, in particular a ligand having a PPPP, NNNN, PNNP or NPPN structure.

Ligands of this type or complexes having such ligands are already known to the person skilled in the art. Reference may be made in this connection, for example, to JP 2003212886, JP 2009073758 or the publications by Tsukada et al. (Tsukada, N.; Tamura, O.; Inoue, Y.; Organometallics 2002, 21, 2521 and Hounjet et al. (Hounjet, L. J.; Bierenstiel, M.; Ferguson, M. J.; McDonald, R.; Cowie, M.; Dalton Trans. 2009, 4213), in which PNNP or NPPN complexes of the metals platinum, rhodium and iridium are described. However, their suitability for opto-electronic applications has to date not been discussed anywhere.

In the case of the tetradentate ligands having N and/or P donors of the general structure PPPP, NNNN, PNNP or NPPN, the two outer P's or N's are generally bonded to the adjacent P or N via a bridge comprising two atoms. The two PP or NN donors in the centre are generally coupled to one another via a bridge comprising one atom. Connecting members between the outer P or N donors and the adjacent donors are preferably C atoms, and carbon, silicon, boron, oxygen or sulfur preferably serves as bridge between the centrally arranged N-N and P-P donors.

The two atoms between the outer P or N donors and the adjacent donors are preferably part of a ring system, in particular a benzene ring. Alternatively, the two bridge atoms may also be constituent of an alicyclic or heterocyclic ring system. Aromatic heterocyclic ring systems are also suitable here. Connections via two atoms connected by means of a double bond are likewise conceivable.

The tetradentate ligand preferably has the general formula I:

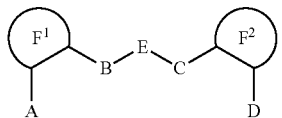

In this structure, the variables are preferably defined as follows:

A, B, C and D are, independently of one another, nitrogen (N) or phosphorus (P), where it is preferred for A and D to be nitrogen and for B and C to be phosphorus (corresponding to the general structure NPPN) or for A and D to be phosphorus and for B and C to be nitrogen (corresponding to the general structure PNNP). The valences of N or P may be at least partially saturated by one or two atom(s) and/or radical(s), in particular from the group comprising hydrogen, halogen, R—, RO—, RS—, RCO—, RCOO—, RNH—, $R_2N$—, RCONR— and —$Si(R)_x(OR)_{3-x}$, where R=a $C_1$-$C_{40}$-hydrocarbon and X=1, 2 or 3.

E is a bridge atom from the group with oxygen, sulfur, carbon, silicon or boron. The valences of these atoms are optionally saturated by one or two atom(s) and/or radical(s), in particular from the group with hydrogen, halogen, —CN, R—, RO—, RS—, RCO—, RCOO—, RNH—, $R_2N$—, RCONR— and —$Si(R)_x(OR)_{3-x}$, where R=the $C_1$-$C_{40}$-hydrocarbon and X=1, 2 or 3.

$F^1$ and $F^2$ are ring systems of an aromatic or non-aromatic nature, where two adjacent ring atoms form the bridge between A and B and between C and D.

In preferred embodiments, the bridge atom E and the two centrally arranged donors B and C may be part of a delocalised electron system, for example in the manner of a heteroallyl system. The delocalisation of the electrons may optionally also extend to the adjacent ring systems $F^1$ and $F^2$ and to A and D or their bonded radicals and to radicals bonded to E if these contain conjugated double bonds or are of an aromatic nature. Correspondingly, it may also be preferred for the two centrally arranged donors B and C to carry no further substituents.

In preferred embodiments, B, C and/or E may carry a negative or positive charge, which may optionally be delocalised. One such embodiment is taken into account by formula III, which is explained in greater detail below.

In preferred embodiments, the tetradentate ligand has the formula II:

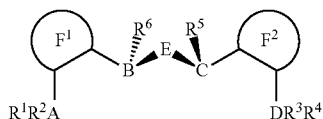

In this structure, the variables are preferably defined as follows:

A, B, C, D, $F^1$ and $F^2$ are defined as in formula I, $R^1$ to $R^6$ are, if they are bonded to a phosphorus, independently of one another, an atom or a radical from the group comprising hydrogen, a halogen, R—, RO—, RS—, RCO—, RCOO—, RNH—, $R_2N$—, RCONR— and —$Si(R)_x(OR)_{3-x}$, where R=the $C_1$ to $C_{40}$ hydrocarbon and X=1, 2 or 3, $R^1$ to $R^6$ are, if they are bonded to a nitrogen, independently of one another, an atom or a radical from the group with hydrogen (H), the $C_1$-$C_{40}$-hydrocarbon R and the silyl radical —$Si(R)_x(OR)_{3-x}$, E is a bridge atom from the group with oxygen, sulfur, carbon, silicon or boron, where
one or two atoms and/or radicals from the group with hydrogen, halogen, —CN, R—, RO—, RS—, RCO—, RCOO—, RNH—, $R_2N$—, RCONR— and —$Si(R)_x(OR)_{3-x}$, where R=the $C_1$-$C_{40}$-hydrocarbon and X=1, 2 or 3, are optionally bonded to the carbon,
two radicals R— and/or RO—, where R=the $C_1$-$C_{40}$-hydrocarbon, are optionally bonded to the silicon or
one or two atoms and/or radicals from the group with halogen, R—, RO—, RS—, RCO—, RCOO—, RNH—, $R_2N$—, RCONR— and —$Si(R)_x(OR)_{3-x}$, where R=the $C_1$-$C_{40}$-hydrocarbon and X=1, 2 or 3, are optionally bonded to the boron.

If the bridge atom E in formula II is a trivalent carbon atom, a carbanion is present. In the case of a tetravalent boron atom, a borate anion is present. The negative charges are optionally delocalised. Thus, the bonds between A, $F^1$, B, E, C, $F^2$ and D are in no way necessarily pure single bonds.

In a preferred embodiment, the tetradentate ligand has the formula III already mentioned, in which the centrally arranged N and/or P donors together with the bridge atom E are part of a delocalised electron system. This electron distribution is indicated in formula III by means of the dashed lines between B and E or C and E. As already mentioned above, the ring systems $F^1$ and $F^2$ as well as A and D may also be involved in the delocalisation of the electrons:

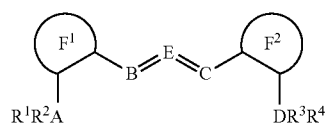

In this structure, the variables are preferably defined as follows:

A, B, C, D, $R^1$ to $R^4$, $F^1$ and $F^2$ are defined as in formula II and

E is a carbon atom, where an atom or radical from the group with hydrogen, halogen, —CN, R—, RO—, RS—, RCO—, RCOO—, RNH—, $R_2N$—, RCONR— and —$Si(R)_x(OR)_{3-x}$, where R=the $C_1$-$C_{40}$-hydrocarbon and X=1, 2 or 3, is optionally bonded to the carbon.

In further preferred embodiments, the tetradentate ligand may have a structure in which only one of the centrally arranged donors B and C forms a delocalised electron system together with the bridge atom E and optionally with participation of a ring system $F^1$ or $F^2$ as well as A or D.

Correspondingly, it may be preferred for only one of the two centrally arranged donors B and C to carry one of the substituents $R^5$ or $R^6$ (see above).

The $C_1$- to $C_{40}$-hydrocarbon R is preferably an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical.

In preferred embodiments, each of these radicals may have one or more halogen, hydroxyl, thiol, carbonyl, keto, carboxyl, cyano, sultone, nitro, amino and/or imino functions.

The expression alkyl radical relates, in particular, to a saturated, straight-chain or branched hydrocarbon group which has 1 to 20 carbon atoms, preferably 1 to 12 carbon atoms, particularly preferably 1 to 6 carbon atoms. Examples thereof are the methyl, ethyl, propyl, isopropyl, isobutyl, t-butyl, n-hexyl, 2,2-dimethylbutyl or n-octyl group.

The expressions alkenyl and alkynyl radical relate, in particular, to at least partially unsaturated, straight-chain or branched hydrocarbon groups which have 2 to 20 carbon atoms, preferably 2 to 12 carbon atoms, particularly preferably 2 to 6 carbon atoms. Examples thereof are the ethenyl, allyl, acetylenyl, propargyl, isoprenyl or hex-2-enyl group.

The expressions cycloalkyl, cycloalkenyl and cycloalkynyl radical relate, in particular, to saturated or partially unsaturated cyclic groups which have one or more rings which have, in particular, 3 to 14 ring carbon atoms, particularly preferably 3 to 10 ring carbon atoms. Examples thereof are the cyclopropyl, cyclohexyl, tetralin or cyclohex-2-enyl group.

The expression heteroalkyl radical relates, in particular, to an alkyl, an alkenyl or an alkynyl group in which one or more (preferably 1, 2 or 3) carbon atoms or CH or $CH_2$ groups have been replaced by an oxygen, nitrogen, phosphorus and/or sulfur atom. Examples thereof are alkyloxy groups, such as methoxy or ethoxy, or tertiary amine structures.

The expression heterocycloalkyl radical relates, in particular, to a cycloalkyl, cycloalkenyl or cycloalkynyl group in which one or more (preferably 1, 2 or 3) ring carbon atoms or ring CH or $CH_2$ groups have been replaced by an oxygen, nitrogen, phosphorus and/or sulfur atom, and can stand, for example, for the piperidine or N-phenylpiperazine group.

The expression aryl radical relates, in particular, to an aromatic group which has one or more rings which contain, in particular, 5 or 6 to 14 ring carbon atoms, particularly preferably 5 or 6 to 10 ring carbon atoms. Examples thereof are a phenyl, naphthyl or 4-hydroxyphenyl group.

The expression heteroaryl radical relates, in particular, to an aryl group in which one or more (preferably 1, 2 or 3) ring carbon atoms or ring CH or $CH_2$ groups have been replaced by an oxygen, nitrogen, phosphorus and/or sulfur atom. Examples thereof are the 4-pyridyl, 2-imidazolyl or the 3-pyrazolyl group.

The expressions aralkyl or heteroaralkyl radical relate, in particular, to groups which, in accordance with the above definitions, contain both aryl and/or heteroaryl groups and also alkyl, alkenyl, alkynyl or heteroalkyl groups. Examples thereof are arylalkyl, arylalkenyl, arylalkynyl, arylheteroalkyl, arylheteroalkenyl, arylheteroalkynyl, heteroarylheteroalkyl, heteroarylheteroalkenyl, heteroarylheteroalkynyl, arylcycloalkyl, heteroarylcycloalkyl, arylheterocycloalkyl, heteroarylheterocycloalkyl, heteroarylcycloalkenyl, arylcycloalkenyl, arylcycloalkynyl, heteroarylcycloalkynyl, arylheteroalkenyl, heteroarylheteroalkenyl, arylheteroalkynyl, heteroarylheteroalkynyl, heteroarylalkyl, heteroalkenyl and heteroarylalkynyl groups.

The expressions alkylcycloalkyl or heteroalkylcycloalkyl radical relate to groups which, in accordance with the above definitions, contain both cycloalkyl or heterocycloalkyl and also alkyl, alkenyl, alkynyl and/or heteroalkyl groups. Examples of such groups are alkylcycloalkyl, alkynylcycloalkyl, alkynylcycloalkyl, alkylheterocycloalkyl, alkenyl-heterocycloalkyl, alkynylheterocycloalkyl, heteroalkylcycloalkyl, heteroalkenylcycloalkyl, heteroalkylheterocycloalkyl, heteroalkynylheterocycloalkyl, heteroalkynylcycloalkyl, and heteroalkynylheterocycloalkyl groups.

A silyl radical for the purposes of the present invention is taken to mean, in particular, a group of the general formula $Si(R)_x(OR)_{3-x}$ described above, where X=1, 2 or 3, where R is preferably an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical, as has been defined above. Examples of the silyl radicals which may be mentioned are —Si(OMe)$_3$, —SiMe(OMe)$_2$, —SiMe$_2$(OMe), —Si(OPh)$_3$, —SiMe(OPh)$_2$, —SiMe$_2$(OPh), —Si(OEt)$_3$, —SiMe(OEt)$_2$, —SiMe$_2$(OEt), —Si(OPr)$_3$, —SiMe(OPr)$_2$, —SiMe$_2$(OPr), —SiEt(OMe)$_2$, —SiEtMe(OMe), —SiEt$_2$(OMe), —SiPh(OMe)$_2$, —SiPhMe(OMe), —SiPh$_2$(OMe), —SiMe(OC(O)Me)$_2$, —SiMe$_2$(OC(O)Me), —SiMe(O—N=CMe$_2$)$_2$ or —SiMe$_2$-(O—N=CMe$_2$), where the abbreviations Me stand for methyl, Ph for phenyl, Et for ethyl and Pr for iso- or n-propyl.

$F^1$ and/or $F^2$ are preferably a cycloalkyl group, cycloalkenyl group, cycloalkynyl group, aryl group, heteroaryl group, aralkyl group and/or a heteroaralkyl group in accordance with the above definition.

In particularly preferred embodiments, A and/or D are ring atoms of a ring system of an aromatic or non-aromatic nature. In this case, $R^1$ and $R^2$ as well as $R^3$ and $R^4$ in the formulae II or III are each fragments of the corresponding ring system. $R^1$, $R^2$ and A and/or $R^3$, $R^4$ and D then preferably form a heterocycloalkyl, heteroaryl, heteroaralkyl or heteroalkylcycloalkyl radical or at least part of one such as is described above. Examples thereof are 5- and 6-membered ring systems, as depicted below, where hydrogen, halogen or the $C_1$- to $C_{40}$-hydrocarbon R described above are preferably in the formulae R', R", R'", independently of one another:

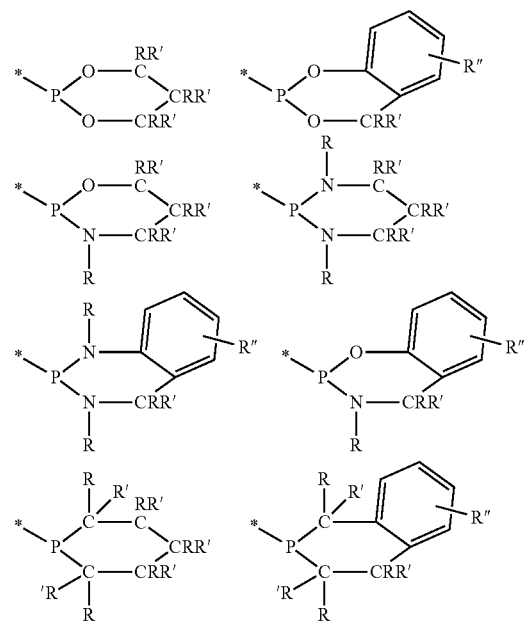

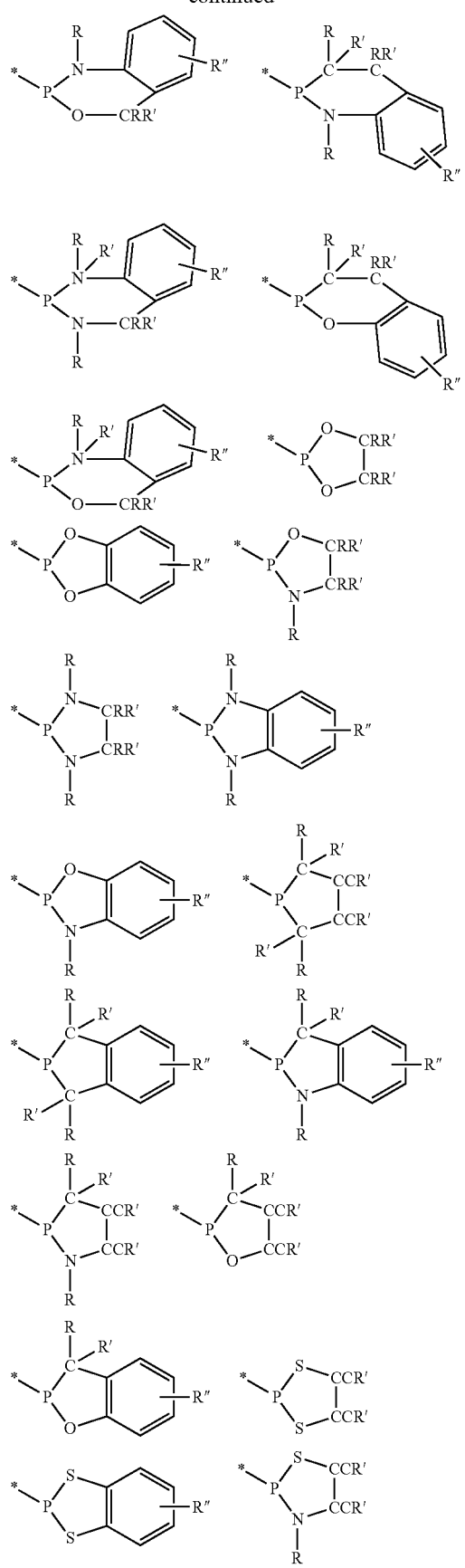
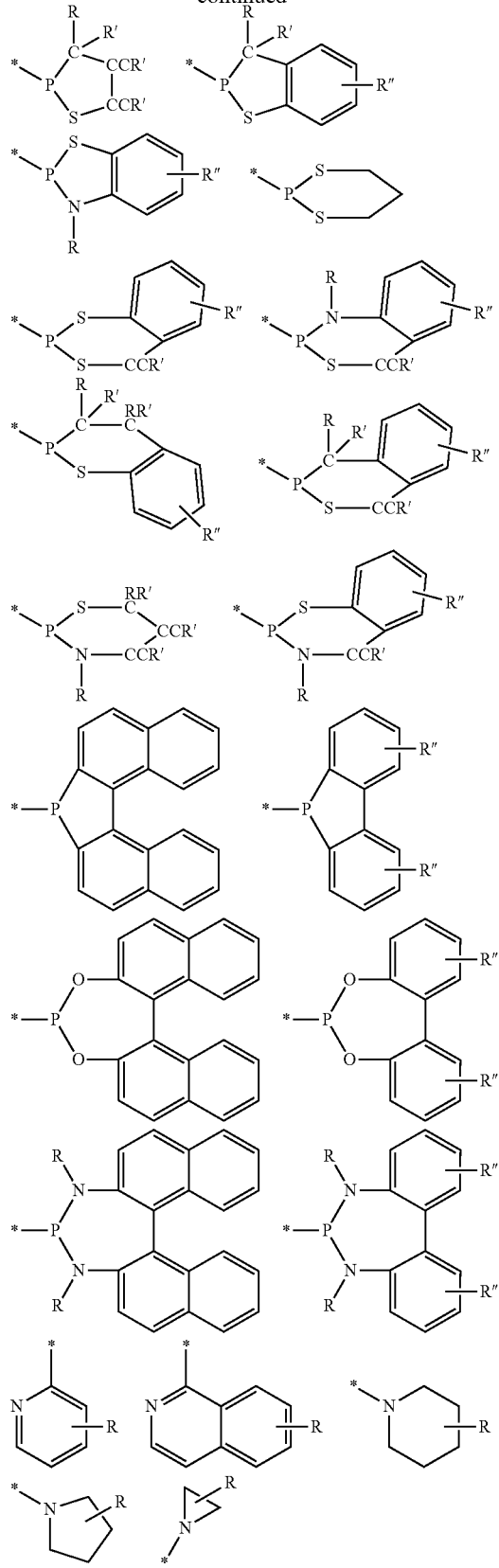
It should be noted here that the ring systems depicted are bonded to $F^1$ and/or $F^2$ via the bond denoted by "*".

In principle, the metal complex can be a mononuclear or polynuclear metal complex. The metal complex preferably has between 2 and 6 metal centres.

In principle, the metal complex can be a copper, silver, gold, palladium, platinum, rhodium, iridium, rhenium, osmium, molybdenum, tungsten or zinc complex. The metals are preferably in the form of cations, in particular they are singly to sextuply positively charged. In particularly preferred embodiments, the metal complex contains copper ions as centres.

The electronic device according to the invention particularly preferably comprises metal complexes of the formulae IV and/or V,

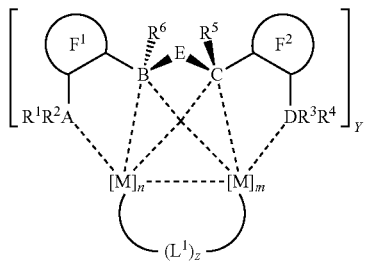

In this formula IV,
A, B, C, D, $R^1$ to $R^6$, E, $F^1$ and $F^2$ are defined as in formula II,
$[M]_m$ and $[M]_n$ are complex fragments where M=Cu, Ag, Au, Pd, Pt, Rh, Ir, Re, Os, Mo, W or Zn and n=0, 1, 2, 3 or a higher integer and m=0, 1, 2, 3 or a higher integer, where the sum of m and n is at least 1,
Y=1, 2, 3 or a higher integer,
Z=0, 1, 2, 3 or a higher integer and
$L^1$=a bridging and/or non-bridging ligand.

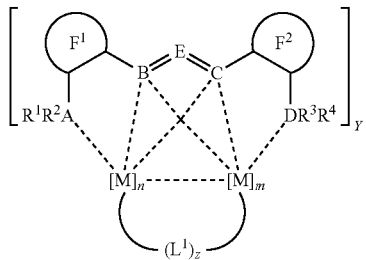

In this formula V,
A, B, C, D, $R^1$ to $R^4$, E, $F^1$ and $F^2$ are defined as in formula III and
$[M]_m$ and $[M]_n$, Y, $L^1$ and Z are defined as in formula IV.

Potential coordination possibilities between the metal centres $[M]_n$ and $[M]_m$ and the donors A, B, C and D are in each case depicted in the formulae IV and V as dashed lines. The dashed line between B and E or C and E in formula V indicates the delocalised electron system described above.

Non-bridging ligands $L^1$ in the present case are intended to be taken to mean ligands which do not bond simultaneously to two or more metal centres. Even though such ligands are not structure-forming, they may have a great influence on the separations between the metal centres of a polynuclear complex in that they increase or reduce the electron densities at the metal centres. The ligands are important for the saturation of the coordination sphere of the metal or for charge equalisation or for both. These ligands $L^1$ can therefore be neutral or anionic. Furthermore, the ligands $L^1$ can be monodentate or bidentate.

Suitable neutral, monodentate ligands $L^1$ are preferably selected from the group with carbon monoxide, nitrogen monoxide, nitriles (RCN), isonitriles (RNC), such as, for example, t-butyl isonitrile, cyclohexyl isonitrile, adamantyl isonitrile, phenyl isonitrile, mesityl isonitrile and 2,6-dimethylphenyl isonitrile, ethers, such as, for example, dimethyl ether and diethyl ether, selenides, amines, such as, for example, trimethylamine, triethylamine and morpholine, imines (RN═CR'), phosphines, such as, for example, triphenylphosphine, phosphites, such as, for example, trimethyl phosphite, arsines, such as, for example, trifluoroarsine, trimethylarsine and triphenylarsine, stibines, such as, for example, trifluorostibine or triphenylstibine, and nitrogen-containing heterocycles, such as, for example, pyridine, pyridazine, pyrazine, pyrimidine and triazine.

Suitable anionic, monodentate ligands $L^1$ are preferably selected from the group with hydride, deuteride, the halides F, Cl, Br and I, azide, alkylacetylides, aryl- or heteroarylacetylides, alkyl, aryl and heteroaryl, as have been defined above, hydroxide, cyanide, cyanate, isocyanate, thiocyanate, isothiocyanate, aliphatic or aromatic alcoholates, such as, for example, methanolate, ethanolate, propanolate and phenolate, aliphatic or aromatic thioalcoholates, such as, for example, methanethiolate, ethanethiolate, propanethiolate and thiophenolate, amides, such as, for example, dimethylamide, diethylamide and morpholide, carboxylates, such as, for example, acetate, trifluoroacetate, propionate and benzoate, anionic, nitrogen-containing heterocycles, such as, for example, pyrrolide, imidazolide, pyrazolide, aliphatic and aromatic phosphides or aliphatic or aromatic selenides.

Suitable di- or trianionic ligands $L^1$ are, for example, $O^{2-}$, $S^{2-}$ or $N^{3-}$.

Neutral or mono- or dianionic bidentate ligands which are suitable as ligand $L^1$ are preferably selected from the group with diamines, such as, for example, ethylenediamine, N,N,N',N'-tetramethylethylenediamine, propylenediamine, N,N,N',N'-tetramethylpropylenediamine, cis- or transdiaminocyclohexane, cis- or trans-N,N,N',N'-tetramethyldiaminocyclohexane, imines, such as, for example, 2-[1-(phenylimino)ethyl]pyridine, 2-[1-(2-methylphenylimino)ethyl]pyridine or 2-[1-(ethylimino)ethyl]pyridine, diimines, such as, for example, 1,2-bis(methylimino)ethane, 1,2-bis(ethylimino)ethane, 1,2-bis(isopropylimino)ethane, 2,3-bis(methylimino)butane, 2,3-bis(isopropylimino)butane or 1,2-bis(2-methylphenylimino)ethane, heterocycles containing two nitrogen atoms, such as, for example, 2,2'-bipyridine or o-phenanthroline, diphosphines, such as, for example, bis(diphenylphosphino)methane, bis(diphenylphosphino)ethane, bis(dimethylphosphino)methane, bis(dimethylphosphino)ethane, bis(diethylphosphino)methane or bis(diethylphosphino)ethane, 1,3-diketonates derived from 1,3-diketones, such as, for example, acetylacetone, benzoylacetone, 1,5-diphenylacetylacetone, dibenzoylmethane and bis(1,1,1-trifluoroacetyl)methane, 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethylglycine, alanine, N,N-dimethylaminoalanine, salicyliminates derived from salicylimines, such as, for example, methylsalicylimine, ethylsalicylimine, phenylsalicylimine, dialcoholates derived from dialcohols, such as, for example, ethylene glycol, 1,3-propylene glycol and dithiolates derived from dithiols, such as, for example, 1,2-ethylenedithiol and 1,3-propylenedithiol.

It is furthermore also possible to employ bidentate monoanionic ligands $L^1$ which, with the metal, have a cyclometallated five-membered ring or six-membered ring having at least one metal-carbon bond, in particular a cyclometallated five-membered ring. These are, in particular, ligands as are generally used in the area of phosphorescent metal complexes for organic electroluminescent devices, i.e. ligands of the phenylpyridine, naphthylpyridine, phenylquinoline, phenylisoquinoline, etc., type, each of which may be substituted or unsubstituted. A multiplicity of such ligands are known to the person skilled in the art in the area of phosphorescent electroluminescent devices, and he will be able to select further ligands of this type as ligand $L^1$ without inventive step.

Bridging ligands $L^1$ in the present case are intended to be taken to mean ligands which bond simultaneously to two or more metal centres and are thus structure-forming. These are thus used, in particular, if the complex used in accordance with the invention is a polynuclear complex. Suitable bridging ligands generally contain at least two donor groups and one bridge fragment connecting the donor groups. The donor group is an atom or an atom group which bonds to the metal atom. The two donor groups may be identical or different, i.e. asymmetrical ligands may also be used Bridging ligands $L^1$ may also be either neutral or anionic. In the latter case, either the donor groups carry a negative charge or the bridge fragment.

Neutral, bridging ligands $L^1$ contain as donor groups, in particular, groups from the series with $R_2N-$, $R_2P-$, $R_2As-$, $R_2N-$, $CN-$, $NC-$, $RO-$, $RS-$, $RSe-$ and $RN=$. ("-" or "=" denotes the bonding mode by means of which the donor group is bonded to the bridge, R preferably a $C_1$- to $C_{40}$-hydrocarbon, as has been defined above). Suitable as bridge fragment is likewise a hydrocarbon as has already been described, preferably having a maximum of 6 C atoms.

In the case of anionic, bridging ligands L1, one or both donor groups are negatively charged, or the bridge fragment carries the charge. Frequently used anionic donor groups are: $O-$, $NR-$ or $C\equiv C-$. Examples of anionic, bridging ligands L1 are, for example,

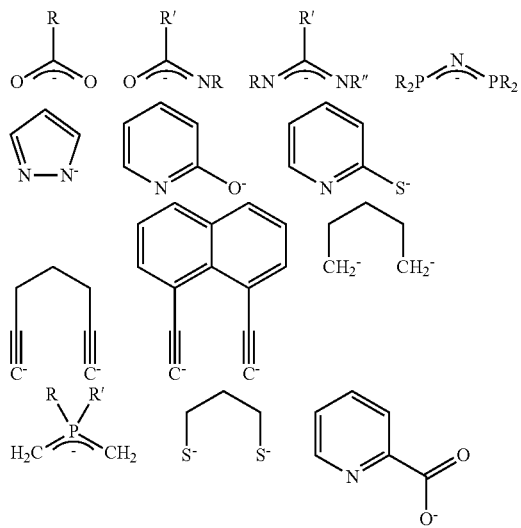

-continued

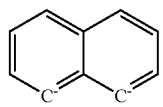

In these formulae, R and R' stand for the $C_1$-$C_{40}$ hydrocarbon defined above.

The metal complexes selected are particularly preferably organic transition-metal compounds which have a ΔE separation between the lowest triplet state and the higher singlet state of between 50 cm$^{-1}$ and 3000 cm$^{-1}$, i.e. have the same properties in this respect as the complexes described in WO 2010/006681. Regarding the calculation or measurement of the energy separation ΔE, reference is made to the statements in this respect in WO 2010/006681.

The device according to the invention is, in particular, a device from the group consisting of organic electroluminescent devices (OLEDs), light-emitting electrochemical cells (LEECs), organic solar cells (OSCs), organic field-effect transistors and organic lasers. Further fields of application which come into question are OLED sensors, in particular gas and vapour sensors which are not hermetically shielded from the outside.

In particular if the electronic device according to the invention is an organic electroluminescent device, it is preferred for the device to comprise the metal complex as constituent of an emitter layer. The proportion of the metal complex in the emitter layer is in this case preferably between 0.1 and 50% by weight.

As is known, OLEDs are built up from a plurality of layers. A layer-like anode, for example consisting of indium tin oxide (ITO), is usually located on a substrate, such as a glass sheet. A hole-transport layer (HTL) is arranged on this anode. A layer of PEDOT/PSS (poly(3,4-ethylenedioxythiophene)polystyrene sulfonate), which serves to lower the injection barrier for holes and prevents indium from diffusing into the junction, may optionally also be located between the anode and the hole-transport layer. The emitter layer, which in the present case comprises the metal complex described above having the at least one tetradentate ligand, is very generally applied to the hole-transport layer. Under certain circumstances, the emitter layer may also consist of this complex. Finally, an electron-transport layer (ETL) is applied to the emitter layer. A cathode layer, for example consisting of a metal or metal alloy, is in turn applied thereto by vapour deposition in a high vacuum. As protective layer and in order to reduce the injection barrier for electrons, a thin layer of lithium fluoride, caesium fluoride or silver may optionally also be applied between cathode and the ETL by vapour deposition.

In operation, the electrons (=negative charge) migrate from the cathode in the direction of the anode, which provides the holes (=positive charge). In the ideal case, holes and electrons meet in the emitter layer, which is why this is also called the recombination layer. Electrons and holes form a bonded state, which is called exciton. A metal complex compound, such as that described in the present case, can be excited by an exciton by energy transfer. This can be converted into the ground state and can emit a photon in the process. The colour of the emitted light depends on the energy separation between excited state and ground state and can be varied in a targeted manner by variation of the complex or complex ligands.

In particular if the device according to the invention is an organic solar cell, it is preferred for the device to comprise the metal complex as constituent of an absorber layer, where the proportion of the metal complex in the absorber layer is preferably between 30 and 100% by weight. An organic solar cell is a solar cell which consists at least predominantly of organic materials, i.e. of hydrocarbon compounds.

As in the case of OLEDs, two electrodes are also provided in organic solar cells. The absorber layer, in which the metal complex described in the present application is used, is arranged between these.

As already mentioned, the metal complex described in the present case can emit light. By variation of the ligands, the LE separation between the lowest triplet state the higher singlet state can be varied, so that it is in principle possible to set the wavelength of the emitted light to defined values, in particular also to very short-wave values, so that blue light is emitted. In particular with copper complexes which have the tetradentate complex ligand described, excellent results have been achieved in this respect. Correspondingly, the present invention also encompasses a process for the generation of light of a certain wavelength or for the generation of blue emission, where in both cases the metal complex described having the tetradentate ligand having N and/or P donors is provided and used.

The complex compounds described are generally very readily soluble in organic solvents, such as benzene or toluene. This opens up the possibility of printing basically any desired substrate with the complex compounds. Correspondingly, the present invention also relates to a process for the production of an electronic device as described above, in which the metal complex compound described having the at least one anionic ligand of the formula I is printed onto a substrate.

Further features of the invention arise from the following description of preferred embodiments. It should be explicitly emphasised at this point that all optional aspects of the devices according to the invention or the processes according to the invention described in the present application can, in an embodiment of the invention, each be achieved individually or in combination with one or more of the further optional aspects described. The following description of preferred embodiments serves merely for explanation and for better understanding of the invention and should in no way be understood as restrictive.

WORKING EXAMPLES

Dinuclear complexes of the metals platinum, rhodium, iridium having the following structural formulae were synthesised in accordance with the experimental procedures in the two above-mentioned publications by Tsukada et al. and Hounjet et al.:

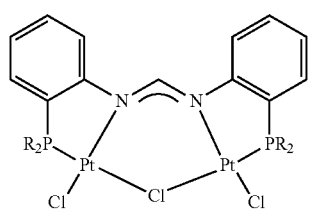

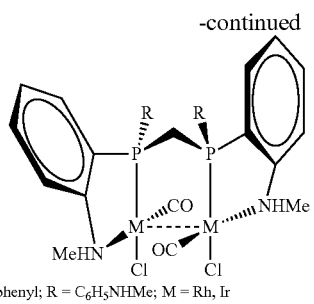

$R_2$ = phenyl; R = $C_6H_5NHMe$; M = Rh, Ir

Furthermore, di-, tri-, tetra- and hexanuclear copper complexes having the following structural formulae were synthesised:

(1) $[Cu_2I_2(CH_2P_2(C_6H_4NMe_2)_4]$—NPPN configuration
(2) $[(C_7N_3H_{13})Cu_3(((Ph)_2PC_6H_4)_2N_2CH)_2Cl]$—PNNP configuration
(3) $[((Ph_2P(o-C_6H_4)N)_2CH)_2Cu_4Cl_2]$—PNNP configuration
(4) $[Cu_6((((CH_3)_2CH)_2PC_6H_4)_2N_2CH)_2Cl_4]$—PNNP configuration
(5) $[Cu_6(((C_6H_{11})_2PC_6H_4)_2N_2CH)_2Cl_4]$—PNNP configuration The complexes were generally prepared by stirring the respective tetradentate ligand with an excess of the respective metal halide in tetrahydrofuran. After filtration, the product was covered with a layer of diethyl ether, and the crystalline product was isolated.

Figure 2:
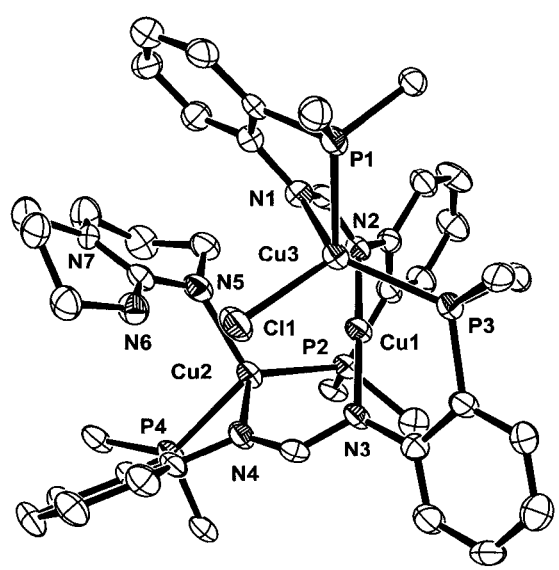
Figure 3:
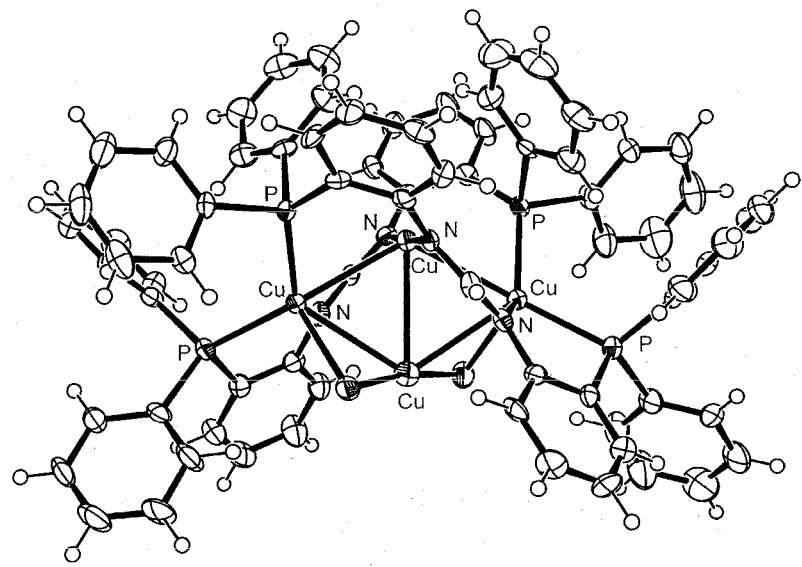
Figure 4:
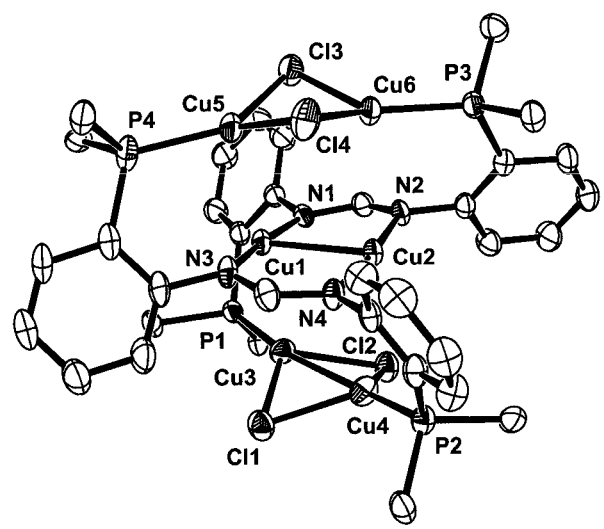
Figure 5:
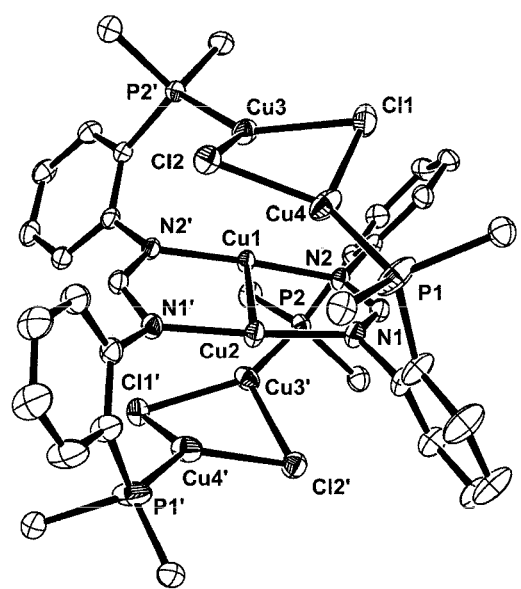

In particular, complexes (1) to (5) exhibited excellent decay behaviour and were easy to prepare. In particular, the tetranuclear copper complex (3) having a PNNP configuration exhibited blue luminescence both as a solid and in solution and also in a polymer matrix (polymethyl methacrylate, PMMA). FIGS. 1 to 5 show the spatial structures of copper complexes (1) to (5) determined by means of X-ray diffractometry:

- The structure of the dinuclear copper complex (1) is depicted in FIG. 1. This complex exhibits an emission at about 515 nm at room temperature in the solid state.
- The structure of the trinuclear copper complex (2) is depicted in FIG. 2. For better clarity, only the ipso-carbon atoms of the phenylphosphine radicals are depicted. This complex exhibits an emission of about 520 nm (on excitation at about 360 nm) at room temperature in toluene.
- The structure of the tetranuclear copper complex (3) is depicted in FIG. 3. This complex exhibits an emission at about 480 nm at room temperature, both in toluene and also embedded in a polystyrene matrix.
- The structure of the hexanuclear copper complex (4) is depicted in FIG. 4. For better clarity, the methyl radicals of the isopropyl groups are not depicted. This complex exhibits an emission at about 550 nm at room temperature, both as a solid and also embedded in a PMMA matrix.
- The structure of the hexanuclear copper complex (5) is depicted in FIG. 5. For better clarity, the methyl radicals on the cyclohexane rings are not depicted. This complex exhibits an emission at about 550 nm at room temperature in the solid state and at 557 nm in PMMA.

The invention claimed is:
1. An electronic device comprising a metal complex having at least one tetradentate ligand having N and/or P donors wherein the ligand has a PPPP, NNNN, PNNP or NPPN structure wherein the ligand has the general formula I

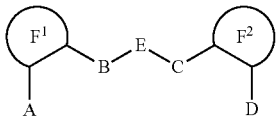

in which
- A, B, C and D are, independently of one another, P or N, where the valences of N or P may be at least partially saturated by one or two atom(s) and/or radical(s),
- E is a bridge atom from the group with oxygen, sulfur, carbon, silicon or boron, to which one or two atom(s) and/or radical(s), and
- $F^1$ and $F^2$ are ring systems of an aromatic or non-aromatic nature, where two adjacent ring atoms form the bridge between A and B and between C and D.

2. The device according to claim 1, wherein the ligand has the formula II

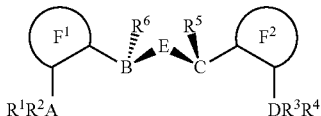

in which
- A, B, C and D are, independently of one another, P or N, where the valences of N or P may be at least partially saturated by one or two atom(s) and/or radical(s),
- $F^1$ and $F^2$ are ring systems of an aromatic or non-aromatic nature, where two adjacent ring atoms form the bridge between A and B and between C and D,
- $R^1$ to $R^6$ are, if they are bonded to a P, independently of one another, an atom or radical from the group comprising hydrogen, a halogen, R—, RO—, RS—, RCO—, RCOO—, RNH—, $R_2$N—, RCONR— and —Si(R)$_x$(OR)$_{3-x}$, where R=the $C_1$-$C_{40}$-hydrocarbon and X=1, 2 or 3,
- $R^1$ to $R^6$ are, if they are bonded to an N, independently of one another, an atom or radical from the group with H, the $C_1$-$C_{40}$-hydrocarbon R and the silyl radical —Si(R)$_x$(OR)$_{3-x}$,
- E is a bridge atom from the group with oxygen, sulfur, carbon, silicon or boron, where
- one or two atoms and/or radicals from the group with hydrogen, halogen, —CN, R—, RO—, RS—, RCO—, RCOO—, RNH—, $R_2$N—, RCONR— and —Si(R)$_x$(OR)$_{3-x}$, where R=the $C_1$-$C_{40}$-hydrocarbon and X=1, 2 or 3, are optionally bonded to the carbon,
- two radicals R— and/or RO—, where R=the $C_1$-$C_{40}$-hydrocarbon, are optionally bonded to the silicon or
- one or two atoms and/or radicals from the group with halogen, R—, RO—, RS—, RCO—, RCOO—, RNH—, $R_2$N—, RCONR— and —Si(R)$_x$(OR)$_{3-x}$, where R=the $C_1$-$C_{40}$-hydrocarbon and X=1, 2 or 3, are optionally bonded to the boron.

3. The device according to claim 1, wherein F1 and/or F2 are a cycloalkyl, cycloalkenyl, cycloalkynyl, aryl, heteroaryl, aralkyl and/or heteroaralkyl radical.

4. The device according to claim 1, wherein A and/or D are ring atoms of a ring system of an aromatic or non-aromatic nature.

5. An electronic device comprising a metal complex having at least one tetradentate ligand having N and/or P donors wherein the ligand has a PPPP, PNNP or NPPN structure and has the formula III

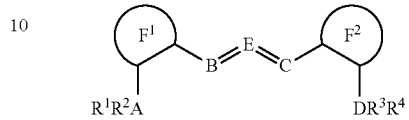

in which
- A, B, C and D are, independently of one another, P or N, where the valences of N or P may be at least partially saturated by one or two atom(s) and/or radical(s),
- $R^1$ to $R^4$ are, if they are bonded to a P, independently of one another, an atom or radical from the group comprising hydrogen, a halogen, R—, RO—, RS—, RCO—, RCOO—, RNH—, $R_2$N—, RCONR— and —Si(R)$_x$(OR)$_{3-x}$, where R=the $C_1$-$C_{40}$-hydrocarbon and X=1, 2 or 3,
- $R^1$ to $R^4$ are, if they are bonded to an N, independently of one another, an atom or radical from the group with H, the $C_1$-$C_{40}$-hydrocarbon R and the silyl radical —Si(R)$_x$(OR)$_{3-x}$,
- $F^1$ and $F^2$ are ring systems of an aromatic or non-aromatic nature, where two adjacent ring atoms form the bridge between A and B and between C and D,
- and E is a carbon atom, where an atom or radical from the group with hydrogen, halogen, —CN, R—, RO—, RS—, RCO—, RCOO—, RNH—, $R_2$N—, RCONR— and —Si(R)$_x$(OR)$_{3-x}$, where R=the $C_1$-$C_{40}$-hydrocarbon and X=1, 2 or 3, is optionally bonded to the carbon.

6. A process for the production of the electronic device according to claim 1, which comprises printing on a substrate a metal complex compound having at least one ligand of the formula I.

7. The device according to claim 1 wherein A, B, C and D are, independently of one another, P or N, where the valences of N or P may be at least partially saturated by one or two atom(s) and/or radical(s), and is selected from the group comprising hydrogen, a halogen, R—, RO—, RS—, RCO—, RCOO—, RNH—, $R_2$N—, RCONR— and —Si(R)$_x$(OR)$_{3-x}$, where R=the $C_1$-$C_{40}$-hydrocarbon and X=1, 2 or 3, and E is a bridge atom from the group with oxygen, sulfur, carbon, silicon or boron, to which one or two atom(s) and/or radical(s), and is selected from the group with hydrogen, halogen, —CN, R—, RO—, RS—, RCO—, RCOO—, RNH—, $R_2$N—, RCONR— and —Si(R)$_x$(OR)$_{3-x}$, where R=the $C_1$-$C_{40}$-hydrocarbon and X=1, 2 or 3, may optionally be bonded.

8. The device according to claim 5, wherein the device comprises the metal complex as constituent of an emitter layer, where the proportion of the metal complex in the emitter layer is between 0.1 and 50% by weight.

9. The device according to claim 5, wherein the C1- to C40-hydrocarbon R is an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical, each of which may have one or more halogen, hydroxyl, thiol, carbonyl, keto, carboxyl, cyano, sulfone, nitro, amino and/or imino functions.

10. The device according to claim 5, wherein the metal complex is mononuclear or polynuclear.

11. The device according to claim 5, wherein the metal complex is a Cu, Ag, Au, Pd, Pt, Rh, Ir, Re, Os, Mo, W or Zn complex or the complex contains at least one of these metals.

12. The device according to claim 5, wherein the device is selected from the group consisting of organic electroluminescent devices (OLEDs), light-emitting electrochemical cells (LEECs), organic solar cells (OSCs), organic field-effect transistors and organic lasers.

13. The device according to claim 5, wherein the device comprises the metal complex as constituent of an absorber layer, where the proportion of the metal complex in the absorber layer is between 30 and 100% by weight.

14. The device according to claim 5, wherein the metal complex is mononuclear or polynuclear and has between two and six metal centres.

15. An electronic device comprising a metal complex having at least one tetradentate ligand having N and/or P donors wherein the ligand has a PPPP, PNNP or NPPN structure and wherein the metal complex has the formula IV or formula V,

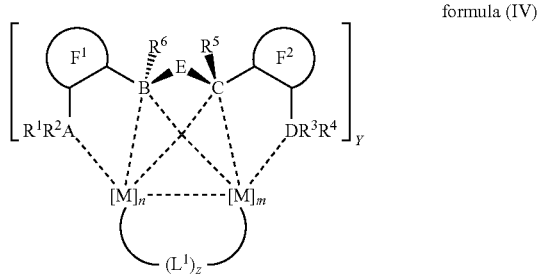

formula (IV)

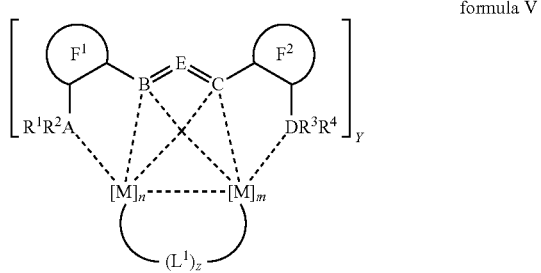

formula V in which

A, B, C and D are, independently of one another, P or N, where the valences of N or P may be at least partially saturated by one or two atom(s) and/or radical(s), $R^1$ to $R^6$ are, if they are bonded to a P, independently of one another, an atom or radical from the group comprising hydrogen, a halogen, R—, RO—, RS—, RCO—, RCOO—, RNH—, $R_2$N—, RCONR— and —Si$(R)_x(OR)_{3-x}$, where R=the $C_1$-$C_{40}$-hydrocarbon and X=1, 2 or 3, $R^1$ to $R^6$ are, if they are bonded to an N, independently of one another, an atom or radical from the group with H, the $C_1$-$C_{40}$-hydrocarbon R and the silyl radical —Si$(R)_x(OR)_{3-x}$ E is a bridge atom from the group with oxygen, sulfur, carbon, silicon or boron, where one or two atoms and/or radicals from the group with hydrogen, halogen, —CN, R—, RO—, RS—, RCO—, RCOO—, RNH—, $R_2$N—, RCONR— and —Si$(R)_x(OR)_{3-x}$, where R=the $C_1$-$C_{40}$-hydrocarbon and X=1, 2 or 3, are optionally bonded to the carbon, two radicals R— and/or RO—, where R=the $C_1$-$C_{40}$-hydrocarbon, are optionally bonded to the silicon or one or two atoms and/or radicals from the group with halogen, R—, RO—, RS—, RCO—, RCOO—, RNH—, $R_2$N—, RCONR— and —Si$(R)_x(OR)_{3-x}$, where R=the $C_1$-$C_{40}$-hydrocarbon and X=1, 2 or 3, are optionally bonded to the boron, $F^1$ and $F^2$ are ring systems of an aromatic or non-aromatic nature, where two adjacent ring atoms form the bridge between A and B and between C and D, $[M]_n$ and $[M]_m$ represent complex fragments where M=Cu, Ag, Au, Pd, Pt, Rh, Ir, Re, Os, Mo, W or Zn and n, m are an integer between 1 and 6, Y is an integer between 1 and 8, $L^1$ is a bridging and/or non-bridging ligand and Z is an integer between 1 and 24.

16. The device according to claim 15, wherein the metal complex has the formula V.

17. The device according to claim 15, wherein the metal complex has the formula IV.

* * * * *